(12) United States Patent
Goodman et al.

(10) Patent No.: US 6,513,813 B1
(45) Date of Patent: Feb. 4, 2003

(54) GEL SLAB SEALING STRIP FOR AN ELECTROPHORESIS TANK

(75) Inventors: Jack Goodman, Lusby, MD (US); N. Leigh Anderson, Washington, DC (US)

(73) Assignee: Large Scale Proteomics Corporation, Germantown, MD (US)

( * ) Notice: Subject to any disclaimer, the term of this patent is extended or adjusted under 35 U.S.C. 154(b) by 0 days.

(21) Appl. No.: 09/576,959

(22) Filed: May 24, 2000

(51) Int. Cl.[7] ................................. F16J 15/02
(52) U.S. Cl. ................. 277/628; 277/637; 277/640; 277/651; 277/906
(58) Field of Search ................ 277/628, 637, 277/640, 644, 648, 651, 906, 910

(56) References Cited

U.S. PATENT DOCUMENTS

| | | | |
|---|---|---|---|
| 3,888,758 A | | 6/1975 | Saeed |
| 4,088,561 A | | 5/1978 | Anderson |
| 4,101,401 A | | 7/1978 | Hoefer |
| 4,159,829 A | * | 7/1979 | Ditcher ................ 277/605 |
| 4,401,538 A | | 8/1983 | Hausfeld |
| 4,495,279 A | * | 1/1985 | Karpetsky et al. ............ 435/18 |
| 4,597,583 A | * | 7/1986 | Inciong et al. ............... 277/591 |
| 4,612,106 A | | 9/1986 | Kromer et al. |
| 4,702,657 A | * | 10/1987 | Jelinek ....................... 411/369 |
| 4,702,814 A | | 10/1987 | Audeh |
| 5,106,477 A | | 4/1992 | Coleman |
| 5,158,661 A | | 10/1992 | Hansen |
| 5,192,408 A | * | 3/1993 | Scott ........................... 204/470 |
| 5,562,813 A | * | 10/1996 | Mullaart et al. ............ 204/466 |
| 5,632,877 A | * | 5/1997 | Van Atta ..................... 204/467 |
| 6,241,253 B1 | * | 6/2001 | Dempsey et al. ........... 277/596 |
| 6,298,908 B1 | * | 10/2001 | Harrell et al. ................ 165/69 |

* cited by examiner

Primary Examiner—Anthony Knight
Assistant Examiner—Michael J Kyle
(74) Attorney, Agent, or Firm—Rothwell, Figg, Ernst & Manbeck (57) ABSTRACT

A gel slab sealing strip adapted for use in an electrophoresis tank is provided according to the invention. The sealing strip includes a body having a height, at least one flap extending outwardly from the body and having a height substantially equal to the body, and a core extending at least partially through the body, wherein the sealing strip is adapted to be inserted into a corresponding receptacle in a bottom of the electrophoresis tank.

41 Claims, 7 Drawing Sheets

FIG. 12

GEL SLAB SEALING STRIP FOR AN ELECTROPHORESIS TANK

BACKGROUND OF THE INVENTION

1. Field of the Invention

The present invention relates generally to an electrophoresis apparatus.

2. Description of the Background Art

Gel electrophoresis is a process for distinguishing and identifying organic macromolecules. Some of the uses of gel electrophoresis are in protein analysis and DNA analysis. Gel electrophoresis typically separates macromolecule components in one or two dimensions to provide a result wherein individual macromolecule components appear as bands or spots. The resulting bands or spots may be analyzed to determine the macromolecule components.

Humans possess a staggering number of such macromolecules that await discovery in order to understand physiological functions and components. In response to this challenge, a wide variety of processes and equipment have been developed to improve the gel electrophoresis process through large-scale automation.

In a first dimension electrophoresis, a test sample is loaded onto a gel and electrophoresed. As a result of the electric field, the macromolecule components in the test sample migrate and become physically separated in one dimension on the basis of their electrical charges.

In the second dimension electrophoresis, the product of the first dimension electrophoresis is further separated on the basis of molecular weight.

The gel slab is typically electrophoresed in a tank holding a buffer fluid. The buffer fluid conducts electricity, with the purpose of the buffer fluid being primarily to form a complete circuit from a first electrode, to a first end of a gel slab (or gel cassette), through the electrophoresis gel, and then from a second end of the gel slab to a second electrode. The gel slab or slabs are therefore desired to be in the path of an electrical current flow between the electrodes, and that the electrical current flow not circumvent the gel slabs. In order to accomplish this, the electrophoresis tank should be constructed so that the buffer fluid in the regions at the ends of the gel slabs are isolated from each other (i.e., fluid tight).

Related art electrophoresis apparatus has typically suffered from a drawback in design of the electrophoresis tank. Related art electrophoresis tanks typically include fixed partitions and seals formed between the fluid in the electrode regions and the region between the gel slabs. Such a configuration may allow fluid leakage, resulting in an electrical current leakage and an uneven or incomplete electrophoresis effect.

There remains a need in the art, therefore, for improvements in electrophoresis processing apparatus.

SUMMARY OF THE INVENTION

A gel slab sealing strip adapted for use in an electrophoresis tank is provided according to a first aspect of the invention. The sealing strip comprises a body having a height, at least one flap extending outwardly from the body and having a height substantially equal to the body, and a core extending at least partially through the body, wherein the sealing strip is adapted to be inserted into a corresponding receptacle in a bottom of the electrophoresis tank.

A gel slab sealing strip adapted for use in an electrophoresis tank is provided according to a second aspect of the invention. The sealing strip comprises a body having a substantially circular cross-section and a height, at least one flap extending outwardly from the body and having a height substantially equal to the body, and a core extending through the body and substantially centered in the body, the core including an exposed core portion extending a predetermined distance outside the body, the core having a rigidity greater than the body, wherein the exposed core portion is adapted to be inserted into a corresponding receptacle in a bottom of the electrophoresis tank.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
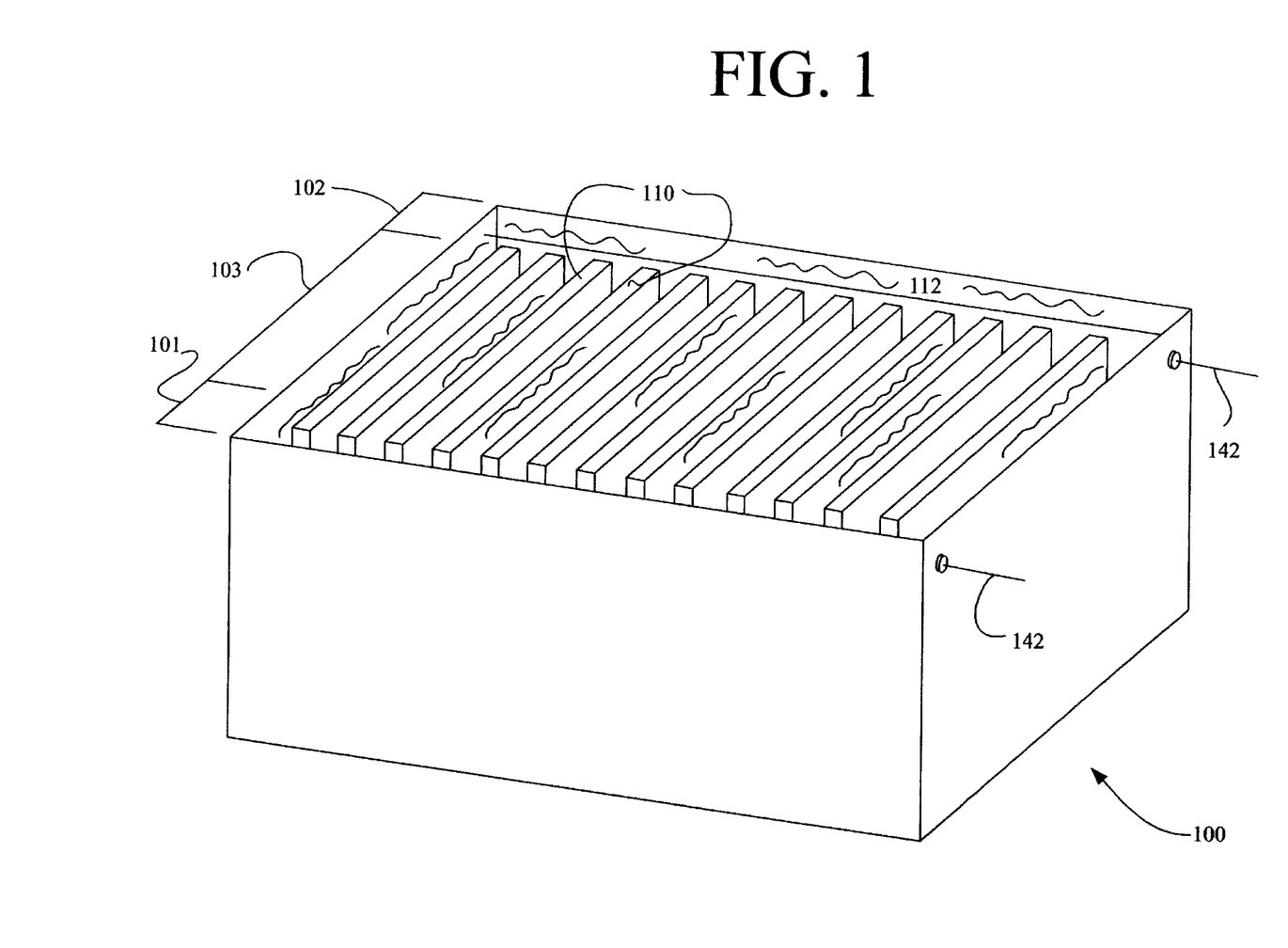
FIG. 1 shows a perspective view of an electrophoresis tank capable of holding a plurality of gel slabs and a volume of buffer fluid.

FIG. 1 shows a perspective view of an electrophoresis tank 100 capable of holding a plurality of gel slabs 110 and a volume of buffer fluid. The buffer fluid is used primarily to conduct electrical current from a pair of electrodes 142 to the plurality of gel slabs 110. As can be seen from the figure, the gel slabs 110 are not fully immersed in the buffer fluid 112. After the plurality of gel slabs 110 have been loaded into the electrophoresis tank 100, an electrical potential may be placed across the electrodes 142, so that the sample macromolecules in the gel slabs 110 will be vertically separated due to the (second dimension) electrophoresis process.

Figure 2:
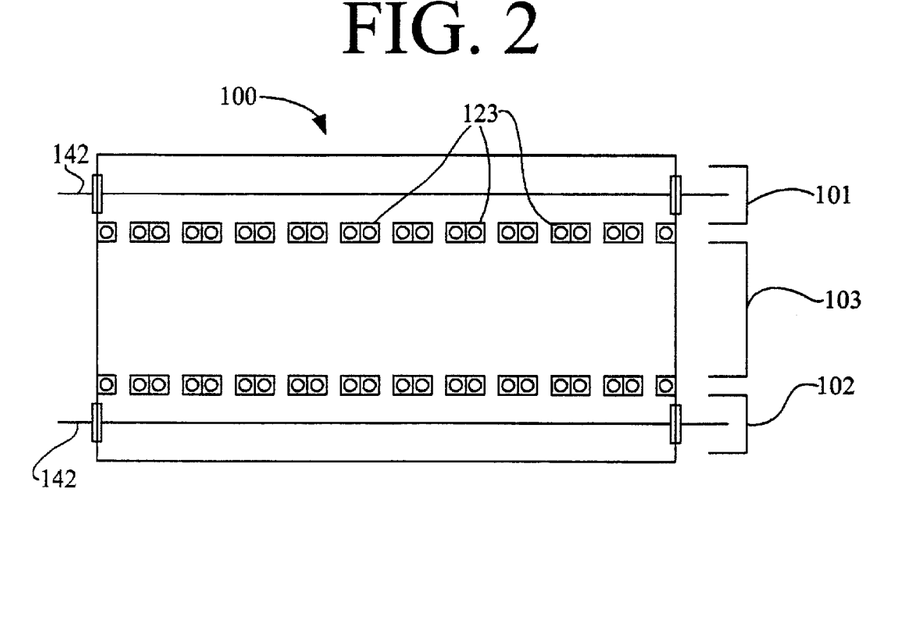
FIG. 2 shows a top view of the electrophoresis tank.

FIG. 2 shows a top view of the electrophoresis tank 100. The electrophoresis tank 100 comprises an outer shell forming a single compartment. The electrophoresis tank 100 includes two electrodes 142. Also included in the electrophoresis tank 100 are a plurality of receptacles 123. The receptacles 123 approximately demarcate the electrophoresis tank 100 into a first region 101, a second region 102, and a third region 103. The third region 103 is disposed between the first region 101 and the second region 102. The receptacles 123 are included in the electrophoresis tank 100 to hold a plurality of sealing strips 302 (discussed below in conjunction with FIG. 3).

Figure 3:
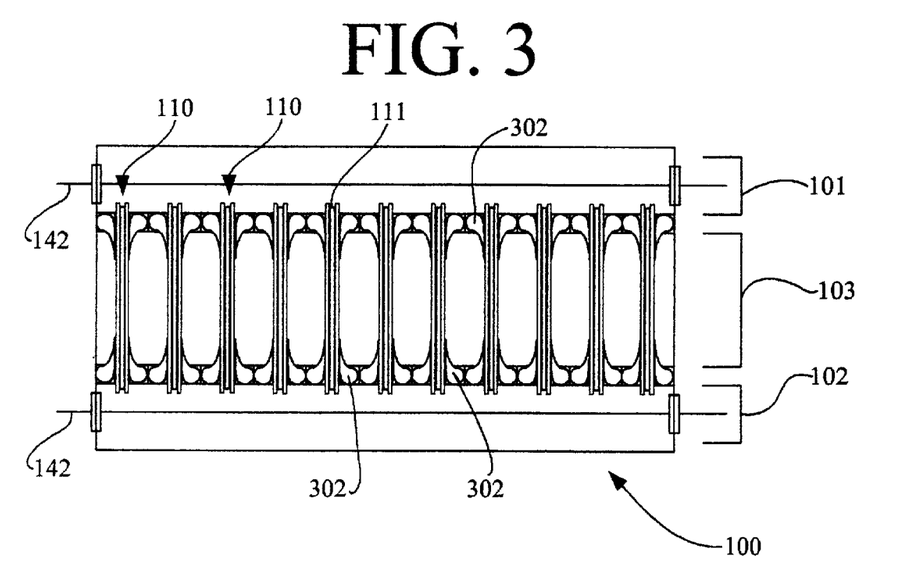
FIG. 3 shows an electrophoresis tank wherein a plurality of gel slabs have been installed between a plurality of sealing strips.

FIG. 3 shows an electrophoresis tank 100 wherein a plurality of gel slabs 110 have been installed between a plurality of sealing strips 302 extending upward from the bottom of the electrophoresis tank 100. As can be seen from the figure, the sealing strips 302 form an essentially fluid tight seal between the gel slabs 110. The result of installing the gel slabs 110 and sealing strips 302 is that the electrophoresis tank 100 is thereby divided up into the first region 101, the second region 102, and the third region 103. Therefore, the buffer fluid is segregated within each region (the gel slabs 110 are generally inserted into the electrophoresis tank 100 after the electrophoresis tank 100 has been filled with buffer fluid). As a result, the ends of the electrophoresis gel 111 of each gel slab 110 are exposed to the first region 101 and the second region 102, and the electrical current is therefore constrained to flow essentially through the electrophoresis gel 111.

Figure 4:
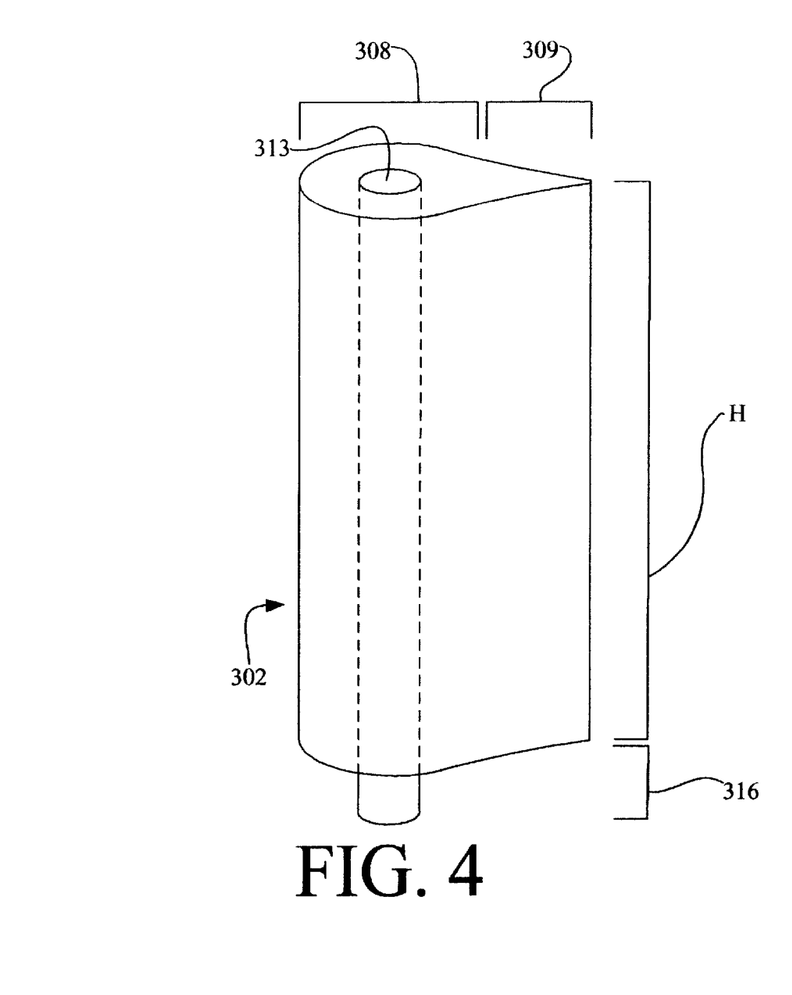
FIG. 4 shows one embodiment of a sealing strip that may be used in the electrophoresis tank of the present invention.

FIG. 4 shows a first embodiment of a sealing strip 302 that may be used in an electrophoresis tank. The sealing strip 302 has a height H, a body 308 having a substantially circular cross-section, and a flap 309 extending from the body 308. The height H is preferably greater than or equal to a height of a gel slab 110.

The sealing strip 302 may be formed in an extruded strip, then cut to length.

The sealing strip 302 is preferably made of silicone rubber, such as RTV, which has excellent dielectric properties as an insulator. However, the sealing strip 302 may be formed of any type of natural or synthetic rubber, resilient resin materials, or of any type of pliable material that is an electrical insulator.

A substantially centered core 313 extends through the body 308. The core 313 has a rigidity greater than a rigidity of the body 308, and may be formed of metal, plastic, etc.

The sealing strip 302 may include an exposed core portion 316 that extends a predetermined distance below the body 308. This exposed core portion 316 is designed to fit into a receptacle 123 of the electrophoresis tank 100. Alternatively, receptacle 123 may have an opening substantially equal to the cross-sectional shape of the sealing strip 302. Therefore, a bottom portion of the sealing strip 302 may fit into the receptacle 123, holding the sealing strip 302 without the need for an exposed core portion.

Figure 5:
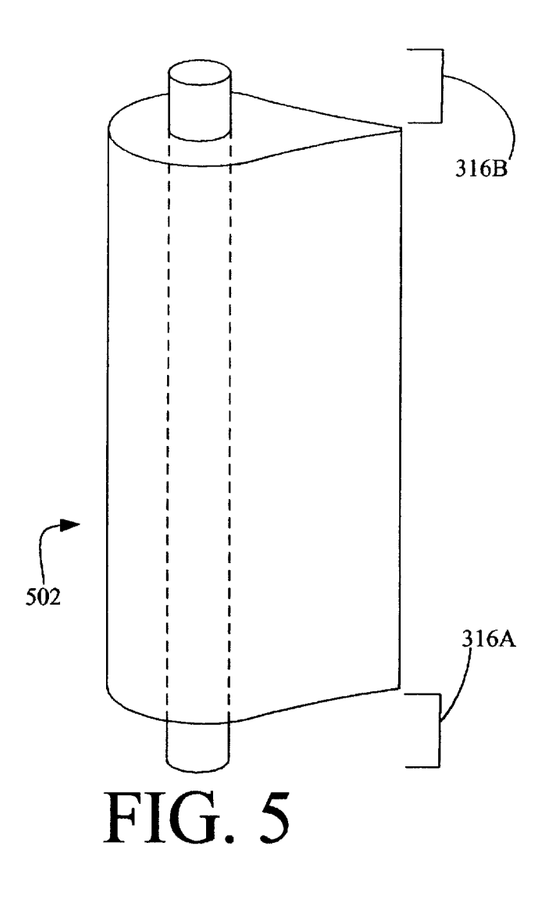
FIG. 5 shows a second embodiment of the sealing strip.

FIG. 5 shows a second embodiment 502 of the sealing strip. The sealing strip 502 includes two exposed core portions 316A and 316B. Therefore, either end of the sealing strip 502 may be inserted into a receptacle 123.

Figure 6:
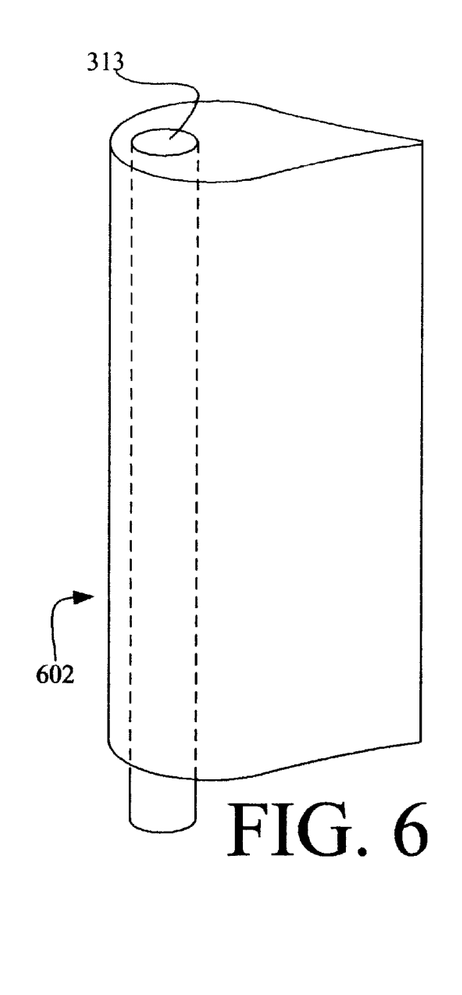
FIG. 6 shows a third embodiment of the sealing strip.

FIG. 6 shows a third embodiment 602 of the sealing strip. In the sealing strip 602, the core 313 is offset from the center of the body 308. Although the figure shows the core 313 being offset away from the flap 309, it should be understood that the core 313 may be offset in any direction from the center of the body 308. An offset may be desirable in order to create a torsional force on the sealing strip 602, counteracting a force exerted by a gel slab 110 (i.e., an offset may prevent rotation of the sealing strip 602).

Figure 7:
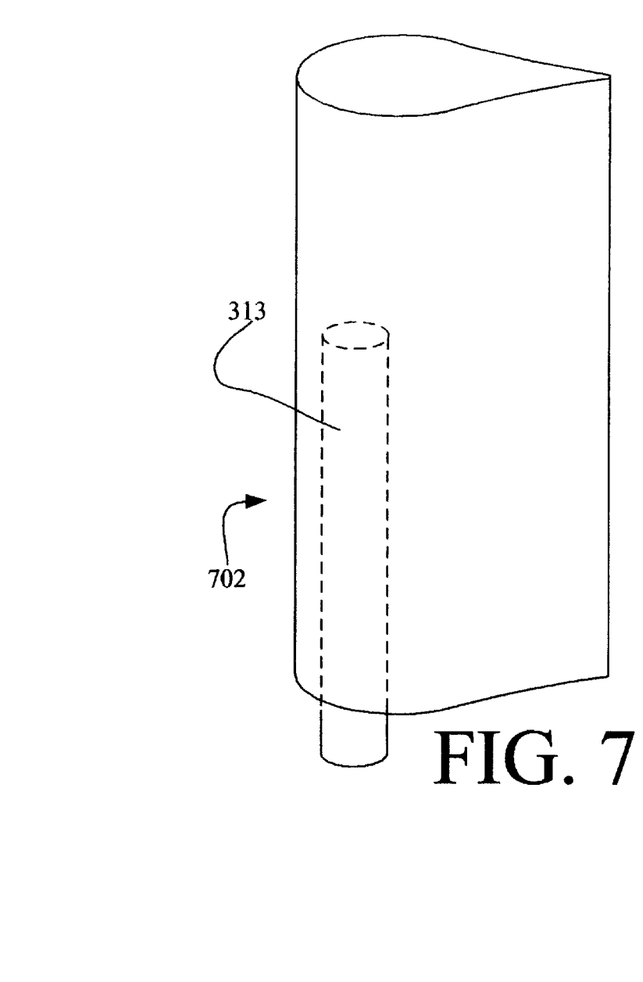
FIG. 7 shows a fourth embodiment of the sealing strip.

FIG. 7 shows a fourth embodiment 702 of the sealing strip. In this embodiment, the core 313 may extend only partially through the body 308.

Figure 8:
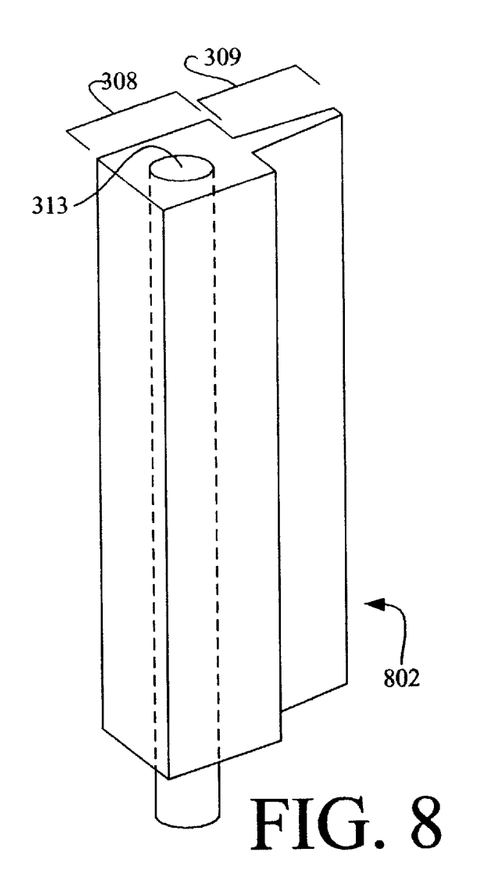
FIG. 8 shows a fifth embodiment of the sealing strip.

FIG. 8 shows a fifth embodiment 802 of the sealing strip. The sealing strip 802 has a body 308 that is substantially rectangular in cross-section. It should be understood from the embodiments shown and described that various other cross-sectional shapes may also be employed, such as oval, triangular, irregular, etc.

Figure 9A:
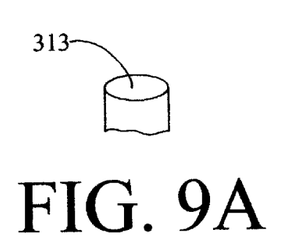
FIGS. 9A–9D show various embodiments of the core.

FIGS. 9A–9D show various embodiments of the core 313. FIG. 9A shows an embodiment wherein the core 313 is substantially circular in cross-section.

Figure 9B:
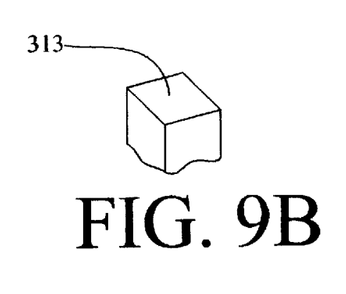

FIG. 9B shows an embodiment wherein the core 313 is substantially rectangular in cross-section.

Figure 9C:
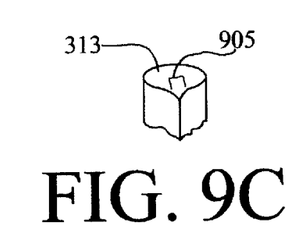

FIG. 9C shows an embodiment wherein the core 313 is substantially circular in cross-section, and further includes at least one height-wise ridge 905. The height-wise ridge 905 may be used to hold the sealing strip 302 in a fixed rotational position in relation to a corresponding receptacle 123.

Figure 9D:
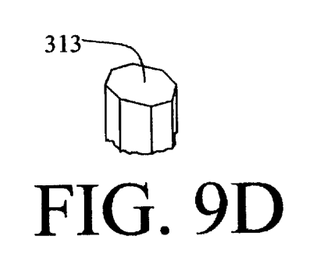

FIG. 9D shows an embodiment wherein the core 313 has a plurality of height-wise planar surface portions, giving the core 313, for example, an octagonal cross-section.

It should of course be understood that a sealing strip 302 may have an exposed core portion 316 (or portions) different in cross-sectional shape from the portion embedded in the body 308.

Figure 10:
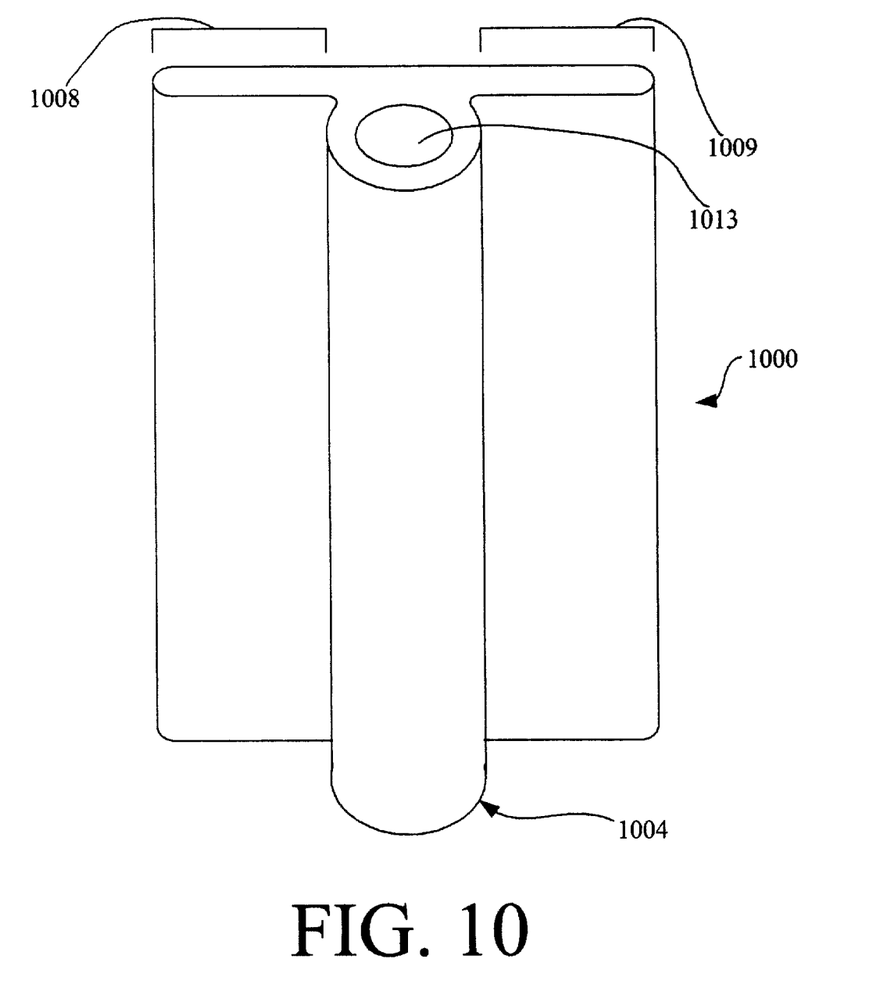
FIGS. 10 and 11 show a sixth embodiment of the sealing strip.
Figure 11:
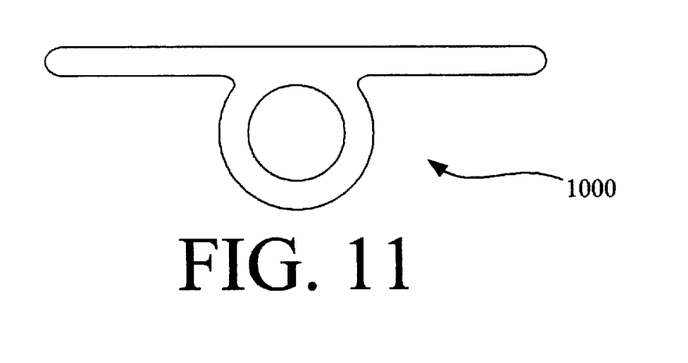

FIGS. 10 and 11 show a sixth embodiment 1000 of the sealing strip. The sealing strip 1000 includes a body 1004 having a substantially circular cross-section and two flaps 1008 and 1009 extending from the body 1004. As in previous embodiments, the sealing strip 1000 may have a core 1013 extending at least partially therethrough.

Figure 12:
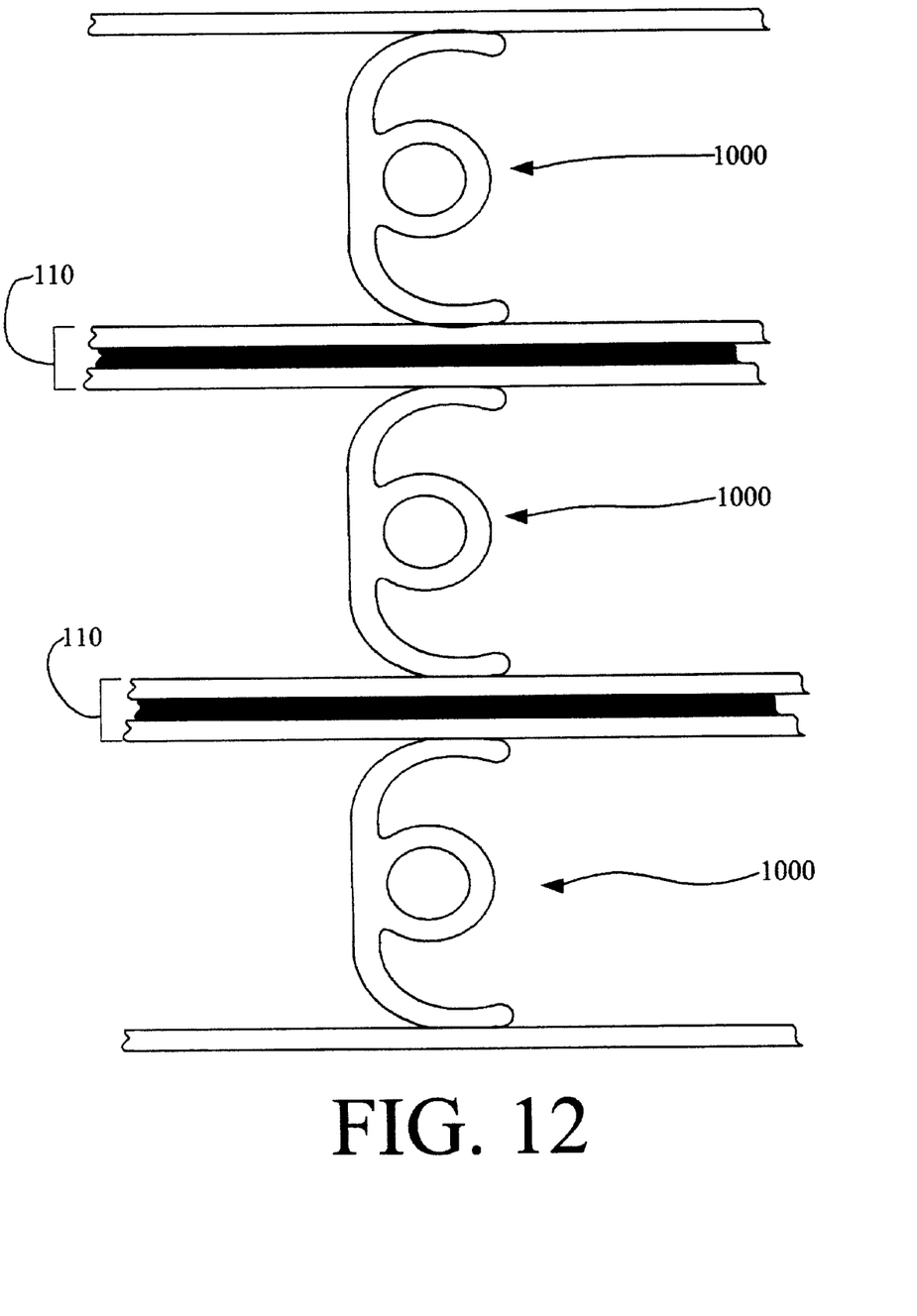
FIG. 12 shows the sealing strip in use.

FIG. 12 shows the sealing strip 1000 in use. One sealing strip 1000 may seal off the space between adjacent gel slabs 110. The span of the flaps 1008 and 1009 exceeds the distance between gel slabs 110 when installed in the electrophoresis tank 100. As in the previous embodiments, the flaps 1008 and 1009 are resilient in nature and are elastically deformed when in position between gel slabs 110. A single sealing strip 1000 may therefore form a barrier to both the buffer fluid and the electrical current.

It should be noted that the sealing strips according to the present invention may be used even when the electrophoresis tank 100 is not full of gel slabs 110. The sealing strips may be placed in the electrophoresis tank 100 in regions without gel slabs 110 to form a barrier to electrical current. This allows a partially full electrophoresis tank to be processed.

It should also be noted that the sealing strips 302, 502, 602, 702 and 1000 are oriented in a generally vertical position in the depicted embodiments to separate the three regions 101, 103 and 102 of the tank 100. Alternatively, the sealing strips 302, 502, 602, 702 and 1000 may be oriented in a horizontal position to separate the regions of the tank. In such an arrangement, the regions 101, 103 and 102 would be one on top of the other, and electrodes 142 would be located at upper and lower portions of the tank 100 such that current flows through the gel slabs 110 from bottom to top or top to bottom of the tank 100.

A sealing strip may employ any combination of the various embodiments discussed above.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A gel slab sealing strip adapted for use in an electrophoresis tank, comprising:
    a body having a height;
    at least one flap extending outwardly from said body and having a height substantially equal to said body; and
    a core extending at least partially through said body;
    wherein only a portion of said core is adapted to be inserted into a corresponding receptacle in a surface of said electrophoresis tank.

2. The sealing strip of claim 1, wherein said sealing strip is comprised of natural or synthetic rubber.

3. The sealing strip of claim 1, wherein said sealing strip is formed of silicone rubber.

4. The sealing strip of claim 1, wherein said body is substantially circular in cross-section.

5. The sealing strip of claim 1, wherein said body is substantially rectangular in cross-section.

6. The sealing strip of claim 1, wherein said at least one flap is tapered.

7. The sealing strip of claim 1, wherein said at least one flap is flexible.

8. The sealing strip of claim 1, wherein said core extends said height of said body.

9. The sealing strip of claim 1, wherein said core includes an exposed portion extending a predetermined distance outside said body, and wherein said exposed core portion is adapted to be inserted into a corresponding receptacle in a bottom of said electrophoresis tank.

10. The sealing strip of claim 1, wherein said core includes an exposed portion at both ends of said body, said exposed core portion extending a predetermined distance outside said body.

11. The sealing strip of claim 1, wherein said core is substantially centered in said body.

12. The sealing strip of claim 1, wherein said core has a rigidity greater than said body.

13. The sealing strip of claim 1, wherein said core is comprised of a metal.

14. The sealing strip of claim 1, wherein said core is comprised of a plastic.

15. The sealing strip of claim 1, wherein said core is substantially circular in cross-section.

16. The sealing strip of claim 1, wherein said core is substantially rectangular in cross-section.

17. The sealing strip of claim 1, wherein said core comprises a plurality of height-wise planar surface portions.

18. The sealing strip of claim 1, wherein said core comprises a plurality of height-wise planar surface portions.

19. The sealing strip of claim 1, wherein said core is rotatable in said corresponding receptacle and said core further includes at least one height-wise ridge, said height-wise ridge being adapted to hold said sealing strip in a fixed rotational position in relation to said corresponding receptacle.

20. The sealing strip of claim 1, wherein said height of said body is at least as great as a gel slab to be inserted in said electrophoresis tank.

21. The sealing strip of claim 1, wherein said at least one flap comprises two flaps extending outwardly from said body.

22. The sealing strip of claim 1, wherein said sealing strip is an electrical insulator.

23. The sealing strip of claim 1, wherein said surface is a bottom of said tank and said sealing strip extends in a vertical direction from said bottom.

24. The sealing strip of claim 1, wherein said surface is a side of said tank and said sealing strip extends in a horizontal direction from said side.

25. A gel slab sealing strip adapted for use in an electrophoresis tank, comprising:
   a body having a substantially circular cross-section and a height;
   at least one flap extending outwardly from said body and having a height substantially equal to said body; and
   a core extending through said body and substantially centered in said body, said core including an exposed core portion extending a predetermined distance outside said body, said core having a rigidity greater than said body;
wherein said exposed core portion is adapted to be inserted into a corresponding receptacle in a surface of said electrophoresis tank.

26. The sealing strip of claim 25, wherein said sealing strip is comprised of natural or synthetic rubber.

27. The sealing strip of claim 25, wherein said sealing strip is formed of silicon rubber.

28. The sealing strip of claim 25, wherein said at least one flap is tapered.

29. The sealing strip of claim 25, wherein said at least one flap is flexible.

30. The sealing strip of claim 25, wherein said core includes an exposed portion at both ends of said body, said exposed core portion extending a predetermined distance outside said body.

31. The sealing strip of claim 25, wherein said core is comprised of a metal.

32. The sealing strip of claim 25, wherein said core is comprised of a plastic.

33. The sealing strip of claim 25, wherein said core is substantially circular in cross-section.

34. The sealing strip of claim 25, wherein said core is substantially rectangular in cross-section.

35. The sealing strip of claim 25, wherein said core comprises a plurality of height-wise planar surface portions.

36. The sealing strip of claim 25, wherein said core is rotatable in said corresponding receptacle and said core further includes at least one height-wise ridge, said height-wise ridge being adapted to hold said sealing strip in a fixed rotational position in relation to said corresponding receptacle.

37. The sealing strip of claim 25, wherein said height of said body is at least as great as a gel slab to be inserted in said electrophoresis tank.

38. The sealing strip of claim 25, wherein said at least one flap comprises two flaps extending outwardly from said body.

39. The sealing strip of claim 25, wherein said sealing strip is an electrical insulator.

40. The sealing strip of claim 25, wherein said surface is a bottom of said tank and said sealing strip extends in a vertical direction from said bottom.

41. The sealing strip of claim 25, wherein said surface is a side of said tank and said sealing strip extends in a horizontal direction from said side.

* * * * *